United States Patent [19]
Steele et al.

[11] Patent Number: 5,484,448
[45] Date of Patent: Jan. 16, 1996

[54] GARMENT AND METHOD FOR COOLING BODY TEMPERATURE

[75] Inventors: Sandra L. Steele, Kingston; Harry W. Nettleton, Hansville, both of Wash.

[73] Assignee: Steele and Associates, Inc., Kingston, Wash.

[21] Appl. No.: 59,239

[22] Filed: May 7, 1993

[51] Int. Cl.⁶ ..................................... A61F 7/00
[52] U.S. Cl. .................... 607/108; 607/109; 607/112; 607/114
[58] Field of Search ............... 607/96, 108–112, 607/114

[56] References Cited

U.S. PATENT DOCUMENTS

| | | |
|---|---|---|
| D. 293,618 | 1/1988 | Berenson . |
| 1,054,426 | 1/1913 | Kuehn et al. . |
| 2,052,684 | 9/1936 | Wisbrod . |
| 2,403,676 | 7/1946 | Modlinski ........................ 607/108 X |
| 2,620,479 | 12/1952 | Buck ..................................... 2/94 |
| 2,748,391 | 6/1956 | Lewis, Jr. et al. . |
| 3,105,241 | 10/1963 | Allen . |
| 3,839,621 | 10/1974 | Hariv ............................ 607/109 X |
| 3,950,789 | 4/1976 | Konz et al. ................... 607/108 X |
| 4,576,169 | 3/1986 | Williams ........................ 128/402 |
| 4,608,717 | 9/1986 | Dunbavand . |
| 4,625,729 | 12/1986 | Roney .............................. 607/114 X |
| 4,637,075 | 1/1987 | Ingrisano et al. ..................... 2/94 |
| 4,697,285 | 10/1987 | Sylvester . |
| 4,887,326 | 12/1989 | O'Brien et al. .................. 607/109 |
| 4,989,267 | 2/1991 | Watson . |
| 5,038,779 | 8/1991 | Barry et al. ...................... 128/402 |
| 5,072,455 | 12/1991 | St. Ours ................................ 2/81 |
| 5,144,694 | 8/1992 | Conrad Da oud et al. ............ 2/69 |
| 5,146,625 | 9/1992 | Steele et al. ........................ 2/102 |
| 5,302,806 | 4/1994 | Simmons et al. ............... 607/108 X |

*Primary Examiner*—Angela D. Sykes
*Attorney, Agent, or Firm*—Seed and Berry

[57] ABSTRACT

A cooling garment including opposed front and back panels to substantially cover a user's torso, a plurality of substantially rectangular elongated pockets affixed to the panels, each of the pockets having a releasably secured opening, and one or more insulating sleeves retaining cooling packs of a size corresponding to the pockets, wherein the cooling pack or packs being confined within the respective elongated pocket or pockets adjacent to a portion of the torso of the user subject to less heat stress are retained in insulating sleeves having a higher insulation value than insulating sleeves retaining cooling packs confined within the pocket or pockets adjacent to a portion of the torso of the user subject to more heat stress, and a method for use of the garment for medical treatment of elevated body temperatures.

19 Claims, 4 Drawing Sheets

GARMENT AND METHOD FOR COOLING BODY TEMPERATURE

DESCRIPTION

1. Technical Field

The present invention relates to a cooling garment, particularly a vest for containing insulated cooling packs, and a medical treatment for cooling body temperature in biophysiologic conditions, including multiple sclerosis and other disorders.

2. Background of the Invention

Many environmental and biophysiologic conditions cause elevated body temperatures. Such conditions often result in discomfort and dehydration, nausea, dizziness, and fainting spells, among other untoward physical signs and symptoms. A variety of industries and climates inflict uncomfortably and, at times, intolerably high temperatures upon persons. For example, heat sources in nuclear plants and foundries emanate heat capable of driving temperatures in such plants up to 120 and 140 degrees Fahrenheit or more. Conditions resulting from heat stress in such environments can increase risk of significant mistakes in judgment, absenteeism and down time.

In addition, many physiological disorders are accompanied by elevations of body temperature; some of those may include multiple sclerosis, trauma patients suffering injury to the spinal cord or brain, and patients with burns, various local, regional, or systemic viral or bacterial infections and other physiological disorders. Further, workers in many industries are required to wear layers of protective clothing to protect against pollutants such as asbestos fibers and radiologic contamination in nuclear plants, which may cause elevation of temperatures and loss of body fluids.

Whether caused by exogenous environmental or intrinsic biogenic factors, or layers of protective clothing, an elevated body temperature may cause great discomfort and lead to serious physical illness or even death.

In the past, various in vivo and in vitro treatments for elevated body temperatures have been used. For example, in cases of severe hyperthermia, ice baths are applied in order to reduce body core temperature. Multiple sclerosis patients have been treated by donning cumbersome suits with tethered tubes through which cooling fluid is circulated with electrical pumps. Keeping the pumps powered and the fluid circulating requires the patient to remain stationed near an electrical outlet or to be accompanied by a generator. Typically, a patient is immobilized during the entirety of the treatment while the cooling agent is applied to the body.

Thus, unfortunately, there are significant limitations and drawbacks with the aforementioned procedures and devices for protecting the body against heat stress and elevated temperatures, including the constriction of movement so as to prevent the user from engaging in normal activities while the ice bath or cooling agent is being applied.

Moreover, known treatments, such as ice baths and the foregoing cooling pump system, utilize systems in which the cooling agent is circulated throughout the application mechanism and, thus, subject a patient's entire torso to a uniformly cool temperature. Known treatment protocols contain no mechanism for restricting the flow of cooling medium in order to facilitate localized application of the cooling mixture commensurate with differing levels of temperature elevation within a patient's body. For instance, there is no mechanism for allowing a patient who feels feverish in the back region, but not in the frontal region, of the torso to confine delivery of a cooling medium to the feverish back area.

In the past, cooling vests have been used to help reduce heat stress caused by high temperatures in industrial facilities. One such vest is described in U.S. Pat. No. 5,146,625, to Steele et al. Unfortunately, however, as with existing treatments for temperature elevations resulting from biologic or physiologic conditions, such vests lack any mechanism for regulation of the extent of cooling delivered to a particular body region so as to vary the extent of cooling commensurately to the degree of discomfort felt by the patient in that particular region of the body. Nor have such vests been utilized in the treatment of heat stress caused by physiologic conditions.

Thus, prior to the present invention, there has been no procedure for external application of cooling agents for treatment of disorders accompanied by elevated body temperatures which does not utilize a cumbersome delivery system severely restricting a patient's movement. To the contrary, previous devices or methods for applying a cooling agent to the torso of a hyperthermic person restrict a user's ability to function and prevents carrying on normal activity. In addition, existing systems have no mechanism for adjusting or varying the extent of cooling delivered to a region or regions of the body, depending upon the degree of heat stress or temperature elevation to which the user is subjected.

SUMMARY OF THE INVENTION

The present invention addresses the foregoing limitations and drawbacks by providing a garment and method of medical treatment for cooling body temperature. In a preferred embodiment of the present invention, a cooling garment includes opposed front and back panels to substantially cover a user's torso, a plurality of substantially rectangular elongated pockets affixed to the front and back panels, each of the pockets having a releasably secured opening, and one or more elongated cooling packs of a size corresponding to the elongated pocket or pockets, each of the cooling packs being confined within respective elongated pockets and being retained within insulating sleeves retaining one or more respective cooling packs. The cooling pack is inserted through and confined within the respective pocket by a releasably secured opening.

An important feature of this cooling garment is the capability to vary the amount of cooling delivered to a particular part of the body in accordance with the degree of heat stress to which it is subject. In the preferred embodiment of the present invention illustrated herein, this variability is achieved, for example, by inserting and retaining a cooling pack into a pocket adjacent to a part of the user's torso which is subject to relatively greater heat stress. An insulating sleeve with an appropriate insulation value is inserted within the pocket to selectively control cooling of the user's torso.

The present invention further includes a method for medical treatment of an elevated body temperature, which in the preferred embodiment illustrated herein includes placing around a user's torso, a cooling garment having a plurality of elongated pockets which confine therein one or more cooling packs of a size corresponding to the elongated pockets.

According to the present invention, the insulating sleeve in which the cooling pack is retained may include a single layer of any suitable material, or may include a structural layer and an insulating layer of any suitable material. Alternatively, the insulating sleeve may include at least one insulating layer sandwiched between at least two structural layers. In a preferred embodiment of the present invention, the insulating sleeve includes an inner layer of nylon tricot and an outer layer of nylon.

Moreover, the plurality of elongated pockets may cover a majority of the portion of the cooling garment covering the torso of the user.

An alternative embodiment of the present invention includes a neck/head cooler, which may be used alone or in conjunction with a cooling garment or vest. The neck/head cooler includes an elongated insulating sleeve confining a corresponding cooling pack such that the neck/head cooler is wrapped around the back and sides of the user's neck or over the head. Alternatively, the neck/head cooler may be releasably secured around the neck/head by a strap with fasteners on each end which are releasably secured to corresponding fasteners on each end of the insulating sleeve. The insulating sleeve of the neck/head cooler may be made of the same layers or materials as the insulating sleeves utilized in the garment or vest of the present invention.

The cooling garment of the present invention is preferably a vest, and may also be a shirt, jacket, neck/head covering, or other article of clothing. In one preferred embodiment of the present invention, the front panel of the cooling vest may include coupling means on the two sides along the central vertical split of the front panel for releasably coupling the front panel together. In any such garment, the plurality of pockets of this cooling garment have inner and outer walls, the outer wall of which may have a greater insulation value than the inner wall.

As previously mentioned, the present invention also provides a method of medical treatment for an elevated body temperature, which includes placing about a patient's torso, a cooling garment having a plurality of elongated pockets confining one or more cooling packs of corresponding size therein. As with the garment of the present invention, the one or more cooling packs may be inserted into an insulating sleeve, such that the extent of cooling delivered by the cooling pack or cooling packs may be reduced.

Hence, the medical treatment for an elevated body temperature includes adjusting the extent of cooling delivered to a region or regions of the torso of a user subjected to varying degrees of heat stress by confining a cooling pack inserted within an insulating sleeve having a higher insulation value within the one or more pockets adjacent to a region or regions of the torso of a user in which there is less heat stress. Conversely, a cooling pack inserted within an insulating sleeve having a reduced insulation value may be confined in the one or more pockets adjacent to the region or regions of the torso of a user in which there is greater heat stress. Thus, a patient suffering degrees of temperature elevation or heat stress in various parts of the torso may be made more comfortable.

Preferred treatment methods of the present invention may further include the step of wrapping the aforedescribed neck/head cooler around the back and sides of the user's neck or over and around the head.

All aspects, features, or embodiments of the aforedescribed garment may also be used in the medical treatment of the present invention. That is, as previously described, the insulating sleeve may be multilayered, and include at least one structural layer and at least one insulating layer; at least one insulating layer sandwiched between at least two structural layers; or include an inner layer of nylon tricot and an outer layer of nylon.

Furthermore, the medical treatment method of the present invention may include, in preferred embodiments, a garment with one or more pockets which have inner and outer walls, the outer walls having a greater insulation value than the inner walls. The medical treatment of the present invention may also contain one or more pockets having outer walls which include at least one structural layer and at least one insulation layer. Alternatively, the outer walls may include at least one structural layer, at least one heat reflective layer, and at least one insulation layer.

DETAILED DESCRIPTION OF THE INVENTION

Figure 1:
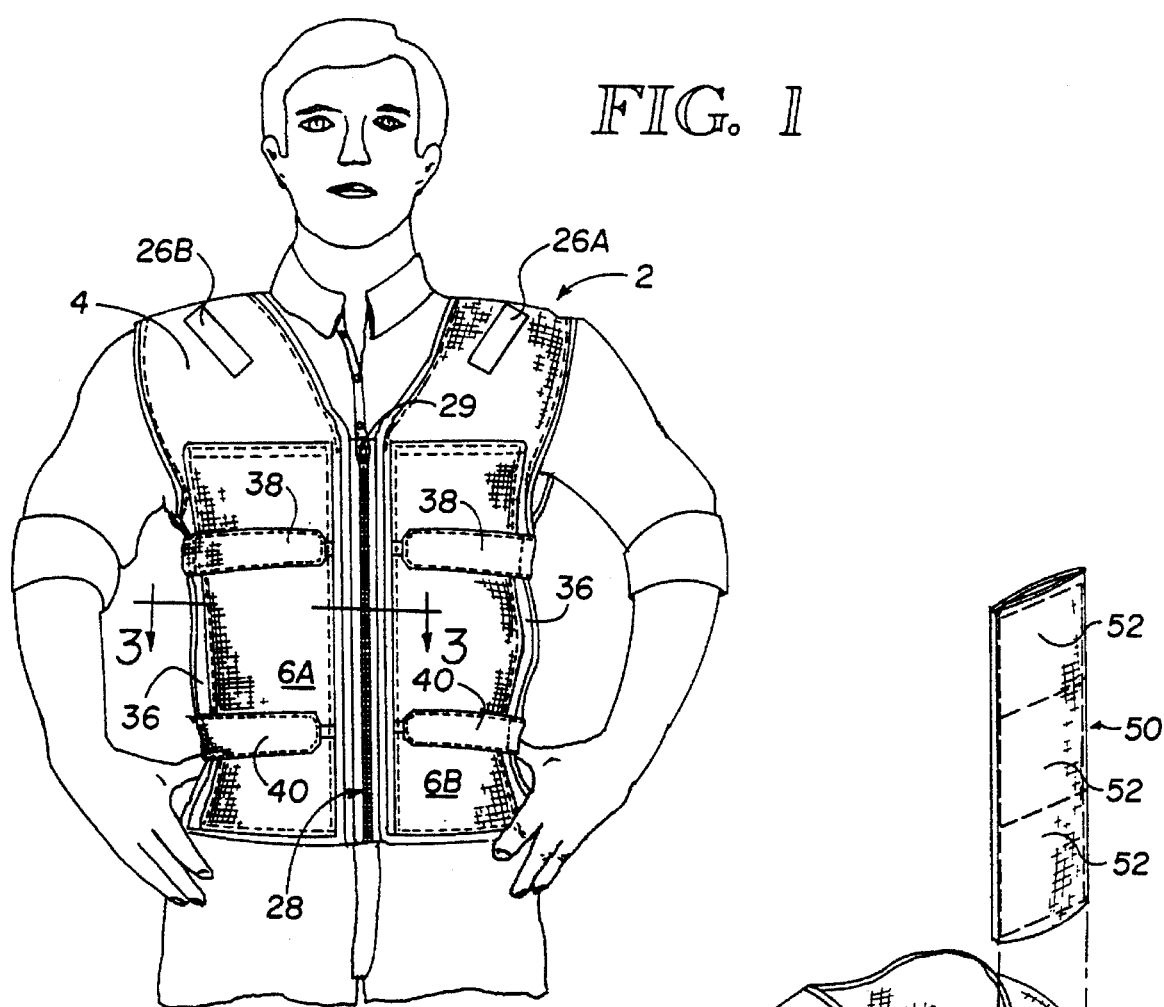
FIG. 1 is a front view of a user wearing a preferred embodiment of the cooling vest of the present invention.
Figure 2:
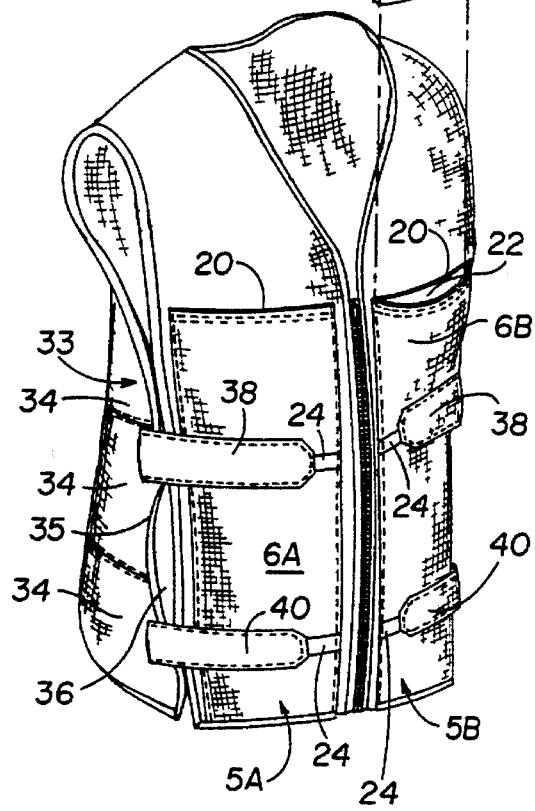
FIG. 2 is a perspective view of the vest of a preferred embodiment of the present invention illustrating an insulating sleeve retaining a cooling pack removed therefrom.

Referring to the drawings, a cooling vest 2 comprising a preferred embodiment of the present invention is shown. The vest 2 has opposed front and back panels 4 and 33, respectively, and split sides 36. The front panel 4 is split into two sections 6a, 6b to define a vertical front opening of the vest 2, which opening is shown in the drawings being fully closed by a coupling means in the form of zipper 28. Sections 6a, 6b of the front panel 4 carry elongated, vertically disposed pockets 6a, 6b which extend over the majority of the area of their respective front panel sections 6a, 6b. Back panel 33 carries elongated, horizontally disposed pockets 34 as seen in FIG. 2. Each front pocket 6a, 6b, and back panel pocket 34 is dimensioned to slidably, and relatively snugly, receive a cooling gel pack 50 as will be described later. Each front pocket 6a, 6b has an opening 20 which is provided with a hook and loop fastener means 22 (the means for only pocket 6b being visible in FIG. 2), such that each opening 20 can be closed to releasably retain a gel pack in its corresponding pocket.

The back panel 33 is provided with three elongated, horizontally oriented pockets 34 which also have hook and loop fastener means (not shown) to releasably close pockets 34. Pockets 34 have similar dimensions to pockets 6a, 6b so that pockets 34 can also relatively snugly receive cooling gel packs of the same type and size as pack 50.

The back panel 33 has two pairs of straps 38, 40 extending from adjacent side edges 35 of back panel 33. Straps 38, 40 and portions 24 of front panel 4 which straps 38, 40 can overlap, carry respective elements of hook and loop fastener means. Such hook and loop fastener means, for convenience of manufacture, may be the same width as the hook and loop fastening means 22 on openings 20 of pockets 22. By the foregoing arrangement, when vest 2 is worn by a user, straps 38 and 40 can be pulled to overlap portions 24 to a sufficient extent to hold vest 2 snugly against the user's body, and held in such position by the hook and loop fastener means. The elongated straps 38, elongated hook and loop fastener means 22 on them, elongated portions of front panel 4, and straps 38, 40 can be adjusted to positions so that vest 2 is adaptable to various sizes and various degrees of tightness in fit. This arrangement, in combination with the split or open sides 36 of vest 2, allows the vest 2 to be snugly fitted on various sizes of users. As already mentioned, zipper 28 acts as a coupling means to allow the vertical front opening of the vest between panel sections 6a, 6b to be opened or closed to various extents as desired by pulling on a zipper tab 29.

Figure 3:
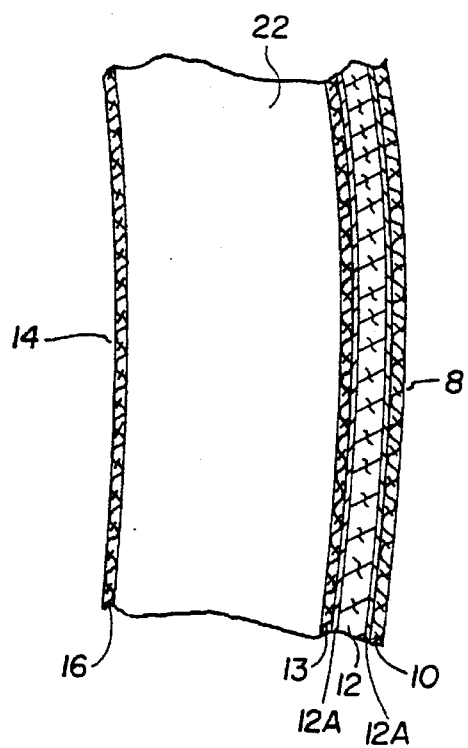
FIG. 3 is a vertical cross section view along line 3—3 of FIG. 1 which illustrates the pocket construction in more detail.

Referring to FIG. 3 in particular, each pocket 6 has inner and outer walls 8, 14, respectively. The outer wall 8 has an outside structural layer in the form of a fabric layer 10 (which is the base material for the vest 2), made of a durable flame-resistant cotton of about 9 ounces/square yard and about 1 mm thickness. Alternatively, the outer wall 8 may be made of a material of a type such as that sold by DuPont Corporation under the trademark NOMEX, which is a flame-retardant ceramic material having a density of about 6 ounces/square yard with about 1 mm thickness. The outer wall 8 also includes insulation in the form of a layer 12 sandwiched between two layers 12a. Layer 12 is an approximately 1 cm thick layer of a fibrous material (65% polyolefin, 35% polyester; 4.6 ounces/square yard), such as that sold by 3M Company under the trademark THINSULATE Type CS50. Layer 12a consists of a layer of metallized polyolefin with holes therethrough to facilitate breathing of vest 2. A suitable material for layers 12a is that sold by Apex Mills, New York, under the trademark TEXOLITE. Outer layer 8 further has a layer 13 made of nylon tricot. It should be noted that the various layers of outer wall 8 extend throughout the vest 2 (except, of course, the inner wall 14). The inner wall 14, on the other hand, has an outside structural layer in the form of fabric layer 16. Fabric layer 16 is preferably of the same material as the layer 10 of the outer wall 8.

Figure 4:
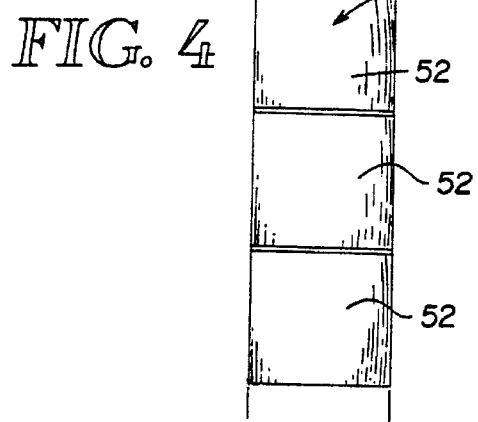
FIG. 4 is an illustration of an insulating sleeve with a cooling pack removed therefrom.

Each gel pack 50 consists of a plastic sheet formed into three individual pouches 52, as best seen in FIG. 4. Each pouch 52 contains a polyethylene bag which in turn contains a gel mixture.

As used herein, a cooling pack may refer to an ice pack or polyethylene pouch containing ice or a gel mixture which has a high heat capacity and thus remains cold for extended periods of time, even at very high temperatures. Such types of gel mixtures are well known for cooling packs for other purposes. A preferred gel composition is one consisting of 100 parts pre gelatinized corn starch, 25 parts of a stabilizing agent such as borax, 800 parts of water, 3 parts of a mold inhibiting agent which may also enhance gel strength, and sufficient soluble mineral salt to lower the freezing point of the gel to approximately 28° F. The gel should have a specific heat of approximately 0.88 and a heat of fusion of approximately 120. The gel should not require more than 170 b.t.u. per pound to freeze it at a temperature of 30° F.

Figure 5:
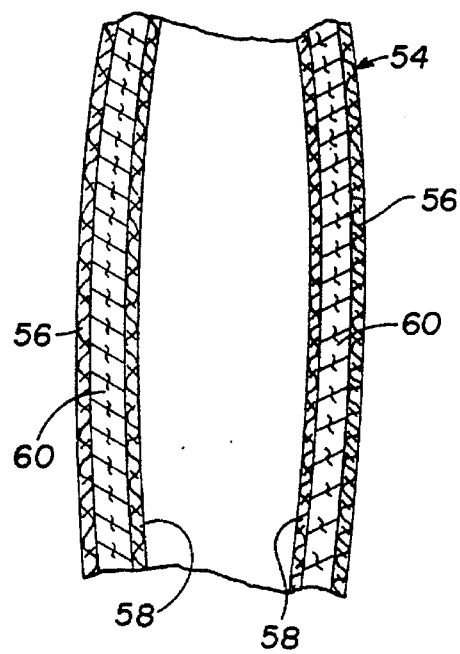
FIG. 5 is a perspective view illustrating a cooling pack with insulation material surrounding it.

Referring to FIGS. 4–5, a cooling pack 50 is enclosed within an insulating sleeve 54, which includes an outer structural layer 56 and which may be made of a durable, flame-resistant cotton, or preferably a nylon. The inner layer 58 may be made of a flame-retardant ceramic material such as NOMEX, or preferably a nylon tricot. The insulating sleeve 54 further includes a center layer 60, which is made of material having a greater insulation value than outer layer 56 and inner layer 58. The center layer 60 may be any suitable insulation material, and is preferably THINSULATE.

The number and composition of layers of insulating sleeve 54 may be varied in order to adjust the extent of the cooling effect emanated from the cooling pack 50 which is inserted therein. Cooling packs 50 may be retained in insulating sleeves 54 having materials of varying insulation values such that different degrees of cooling may be applied to regions of the body that are exposed to different levels of heat stress. Thus, a user may apply the extents of cooling desired to alleviate the degree of discomfort to which a particular region of the body is subject.

For example, a user who is partially exposed to sunlight or another heat source will have greater heat stress or discomfort in the region of the torso directed toward the heat. A lesser degree of heat stress or temperature elevation will, conversely, be exerted upon the portion of the torso directed away from the sunlight or heat source. In order to vary the extent of cooling applied to the hotter frontal region of the torso, the cooling packs 50 inserted into front pockets 6a, 6b may be retained in an insulating sleeve 54 made of material having a relatively lower insulation value of, for example, between about 0.0 R value and about 0.62 R value. The lower insulation value generates a relatively thin shield and thus permits greater cooling to the user's frontal torso. In contrast, cooling packs 50 inserted in rear pockets 34 may be retained in an insulating sleeve 54 made of material having a relatively higher insulation value of, for example, between about 0.62 R value and about 1.14 R value, which permits less cooling to the rear regions of the user's torso.

To use the vest 2 comprising a preferred embodiment of the present invention, five cooling gel packs 50 would first be pre-cooled (preferably frozen) in a freezer. The user, who would normally be wearing at least one layer of clothing, would then insert two of the five gel packs 50 into the openings 6a, 6b on the front panel 4. Hand pressure would then be applied to hook and loop fasteners 22 to close openings 20 and retain the two gel packs in their respective pockets 6a, 6b. In a similar manner, the remaining three gel packs 50 would be inserted and retained in the three horizontal pockets on the back panel 33. Alternatively, the two packs 50 for front pockets 6a, 6b could be inserted therein after the user has donned the vest 2. Prior to donning the vest 2, zipper 28 would typically be in the open position (i.e., the vertical front opening of the vest is open), while hook and loop fasteners between the straps 38, 40 and the portions 24 would be in the unfastened position so that the split sides 36 are also open. The user can then simply slip on the vest 2 from behind. Straps 38, 40 can then be pulled to bring the vest 2 snugly against the user's torso, and straps 38, 40 are held in position by engaging respective hook and loop fasteners between them and the portions 24 which they overlap. It can be seen that due to the elongated construction of the straps 38, 40 and portions 24, and the elongated hook and loop fasteners, all in conjunction with the split sides 36, that vest 2 can be snugly worn by various sized users.

Once the vest has been donned in the foregoing manner, zipper tab 29 will normally be pulled upward to at least partially close the zipper 28 (and hence the front opening of the vest). The zipper 28 need not be closed entirely. The user may select how much outside air will enter the front of the jacket by adjusting the zipper 28. Of course, the position in which the straps 38, 40 are retained could be additionally adjusted to vary air circulation in the vest 2, but this would lead to a loosening of the vest which may be undesirable in certain situations.

When worn as described, the vest 2 can keep the user cool for several hours, depending upon the ambient temperature, humidity, clothing worn, and the user's activity. The closable front opening allows for easy donning and removal of the vest 2 by a user. The various layers of insulation which may be present also allow air circulation and control cooling in a manner fully described in allowed U.S. patent application Ser. No. 07/676,092, to Steele et al., already mentioned.

In addition to the advantages provided by the vertical front opening described, the fact that the pockets 6a, 6b are vertically oriented allows for ready insertion and removal of cooling packs 50, even when vest 2 is still being worn. Also, the straps 38, 40 will provide some assistance in inhibiting sagging of gel packs 50 in pockets 20. The segmenting of gel packs 50 into three segments 52 also limits such sagging and enhances forward flexing ability by a user wearing vest 2 with packs 50 in pockets 20.

In order to remove vest 2, a user simply opens the zipper 28 and pulls outward on the straps 38, 40 to disengage the hook and loop fastener means. The vest 2 may then be slipped off backward from a user's torso.

Figure 6:
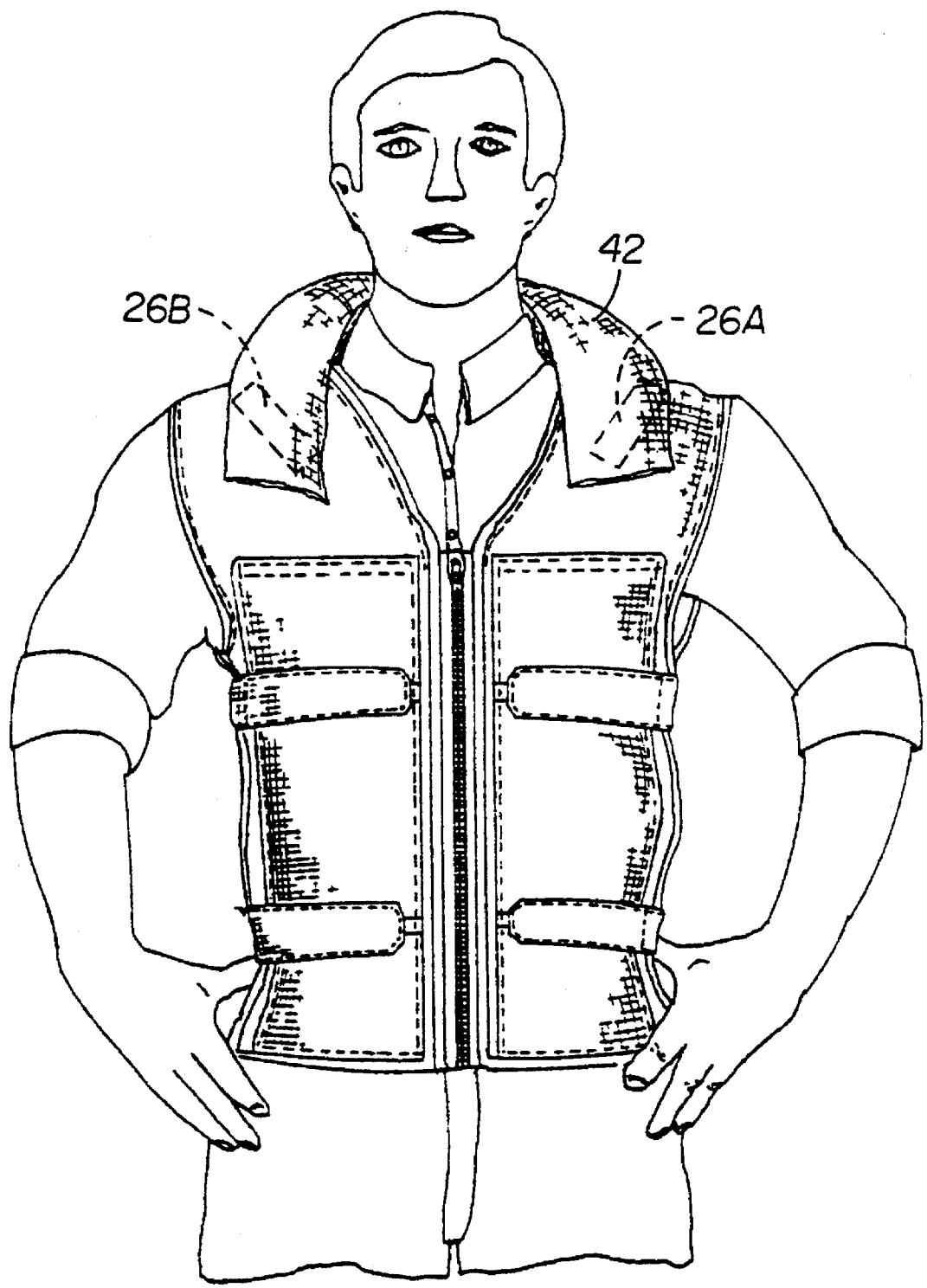
FIG. 6 is a front perspective view of a preferred embodiment of the present invention with a neck/head cooler attached thereto.

Referring to FIG. 6, the neck/head cooler 42 is releasably secured to the vest 2 by hook and loop fastener means 26a and 26b. Hooks or loops 26a and 26b are affixed on both ends of the neck/head cooler 42 and are affixed on the appropriate strip in the frontal shoulder area of the vest 2. Thus, the neck/head cooler 42 may be snugly secured about the user's neck/head as shown. The neck/head cooler 42 may also be worn over and around the head.

Figure 7:
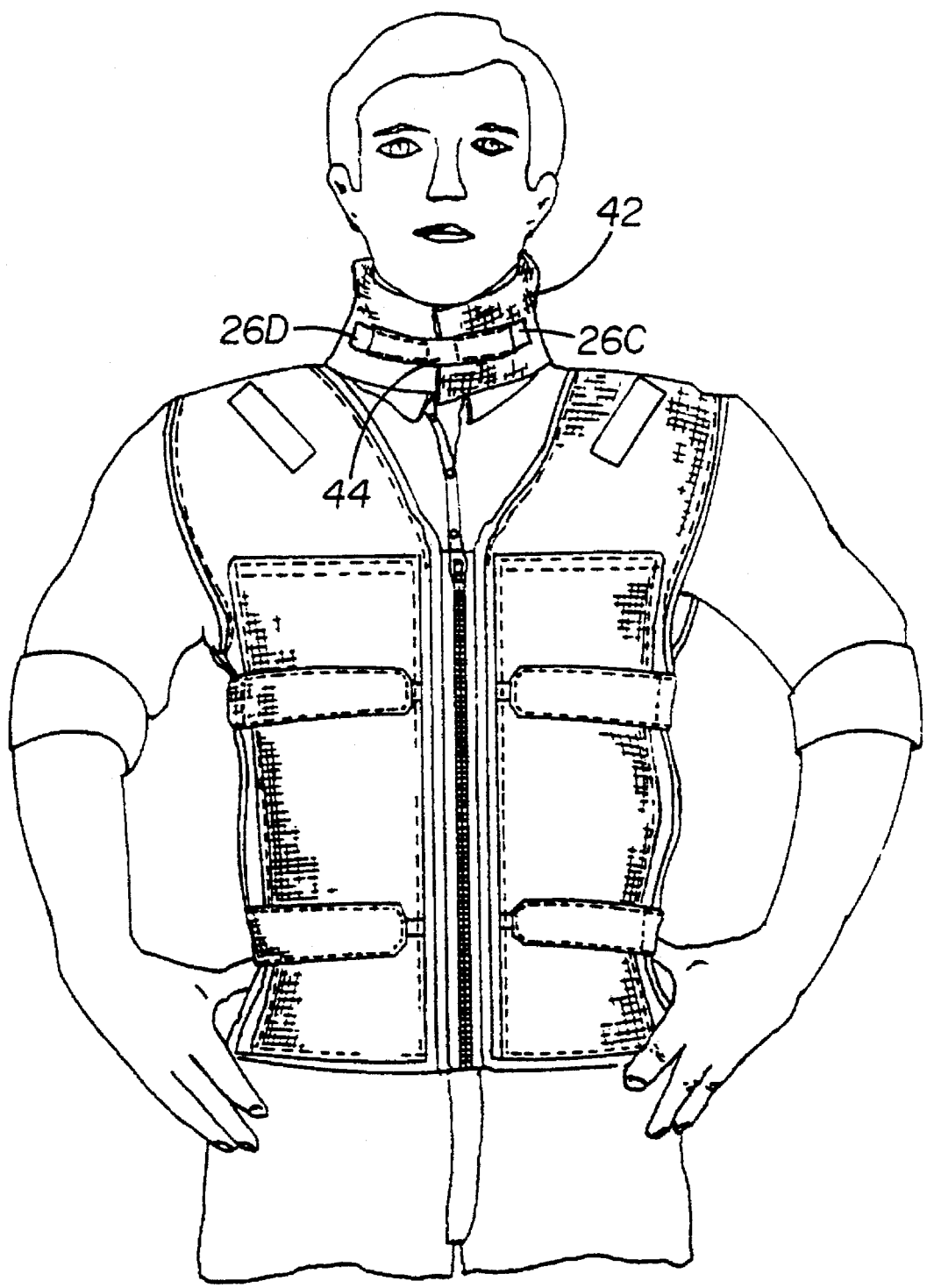
FIG. 7 is a front perspective view of the neck/head cooler secured by fasteners on a strap.

Alternatively, referring to FIG. 7, the neck/head cooler 42 may be independently secured around the user's neck or head region by fastening to the hooks or loops 26c and 26d the stretchable elastic strap 44 having corresponding hooks or loops 26c and 26d attached to both ends thereof.

It will be appreciated that various modifications and alterations can be made to the specific embodiments of the invention described above. Accordingly, the present invention is not limited to the specific embodiments described above but rather is defined by the claims which follow.

We claim:

1. A cooling garment, comprising:
   (a) opposed front and back panels to substantially cover a user's torso;
   (b) a plurality of substantially rectangular elongated pockets affixed to the front and back panels, each of the pockets having a releasably secured opening; and
   (c) one or more insulating sleeves retaining cooling packs of a size corresponding to the elongated pockets, wherein the cooling packs being confined within the pocket or pockets adjacent to a portion of the user's torso subject to less heat stress are retained in insulating sleeves having a higher insulation value than insulating sleeves retaining cooling packs confined within the pocket or pockets adjacent to a portion of the user's torso subject to more heat stress.

2. The cooling garment of claim 1 wherein the insulating sleeve comprises at least one structural layer and at least one breathable insulating layer.

3. The cooling garment of claim 1 wherein the insulating sleeve comprises at least one breathable insulating layer sandwiched between at least two structural layers.

4. The cooling garment of claim 1 wherein the insulating sleeve comprises an inner layer of nylon tricot and an outer layer of nylon.

5. The cooling garment of claim 1 wherein the plurality of the elongated pockets cover a majority of the portion of the cooling garment covering the torso of the user.

6. The cooling garment of claim 1, further comprising a cooler for the neck and head which includes an elongated sleeve having a releasably secured opening and confining a cooling pack, and wherein the neck and head cooler is releasably secured to the upper frontal region of the garment such that the neck and head cooler is wrapped around the back and sides of the user's neck and head region.

7. A cooling garment, comprising:
   (a) opposed front and back panels to substantially cover a user's torso, the opposed front and back panels having an exterior side that faces away from a user's torso;
   (b) a plurality of substantially rectangular elongated pockets affixed to the exterior side of the opposed front and back panels;
   (c) one or more insulating sleeves for retaining cooling packs of a size corresponding to the elongated pockets, each of the insulating sleeves having at least one structural layer and at least one breathable insulating layer, each of the cooling packs being confined within respective elongated pockets; and
   (d) a neck and head cooler which includes an elongated sleeve having a releasably securable opening and confining a corresponding cooling pack, wherein the neck and head cooler is releasably secured to the upper frontal region of the vest such that the neck cooler is wrapped around the back and sides of the user's neck and head region.

8. The cooling garment of claim 7 wherein the insulating sleeve comprises at least one breathable insulating layer sandwiched between at least two structural layers.

9. The cooling garment of claim 7 wherein the insulating sleeve comprises an inner layer of nylon tricot and an outer layer of nylon.

10. The cooling garment of claim 7 wherein the plurality of elongated pockets cover a majority of the portion of the cooling garment covering the torso of the user.

11. The cooling garment of claim 7 wherein one or more of the cooling packs confined within the elongated pocket or pockets adjacent to a portion of the user's torso subject to less heat stress is retained in an insulating sleeve having a higher insulation value than insulating sleeves retaining one or more cooling packs confined within the pocket or pockets adjacent to a portion of the user's torso subject to more heat stress.

12. A method of medical treatment for an elevated body temperature, comprising:
   (a) placing a cooling garment having a plurality of elongated pockets about a user's torso, the cooling vest comprising opposed front and back panels to substantially cover the user's torso, the opposed front and back panels having an interior surface facing toward the user's torso and an exterior surface facing away from the user's torso;
   (b) inserting in a plurality of elongated pockets on the exterior surface of the opposed front and back panels one or more cooling packs of a size corresponding to the one or more elongated pockets with the cooling packs being removable from the elongated packets when the cooling garment substantially covers the user's torso; and
   (c) retaining the one or more cooling packs in a corresponding breathable insulating sleeve prior to confining the cooling pack or packs within one or more of the elongated pockets of the cooling garment such that the extent of cooling delivered to the user's torso by the cooling pack or packs through the front or back panels is reduced wherein the cooling packs being confined within the pocket or pockets adjacent to a portion of the user's torso subject to less heat stress are retained in insulating sleeves having a higher insulation value than insulating sleeves retaining cooling packs confined within the pocket or pockets adjacent to a portion of the user's torso subject to more heat stress.

13. The medical treatment of claim 12, further comprising inserting at least one of the cooling packs into an insulating sleeve which includes at least two layers, one of which is a structural layer.

14. The medical treatment of claim 12, further comprising inserting at least one of the cooling packs into an insulating sleeve which includes at least one breathable insulating layer sandwiched between at least two structural layers.

15. The medical treatment of claim 12, further comprising inserting at least one of the cooling packs into an insulating sleeve which includes an inner layer of nylon tricot and an outer layer of nylon.

16. The medical treatment of claim 12, further comprising retaining a cooling pack or packs within the pocket or pockets adjacent to a portion of the user's torso subject to less heat stress within an insulating sleeve having a higher insulation value than an insulating sleeve retaining a cooling pack or packs confined within the pocket or pockets adjacent to a portion of the user's torso subject to more heat stress.

17. The medical treatment of claim 12 wherein the pockets of the cooling garment have inner and outer walls, the outer walls having a greater insulation value than the inner walls.

18. The medical treatment of claim 12 wherein the pockets of the cooling garment have inner and outer walls, the outer walls comprising at least one structural layer and at least one breathable insulating layer.

19. The medical treatment of claim 12 wherein the front panel of the cooling vest has a coupling means on two sides along the substantially central vertical split of the front panel for releasably coupling the front panels together.

* * * * *